US00H002153H

(19) United States

(12) Statutory Invention Registration

Ignar et al.

(10) Reg. No.: US H2153 H

(43) Published: Apr. 4, 2006

(54) ASSOCIATION OF ASTHMA WITH POLYMORPHISMS IN THE CYSTEINYL LEUKOTRIENE 2 RECEPTOR

(75) Inventors: Diane Michele Ignar, Durham, NC (US); Sreekumar Pillai, Durham, NC (US)

(73) Assignee: SmithKline Beecham Corp., Philadelphia, PA (US)

(21) Appl. No.: 10/131,332

(22) Filed: Apr. 24, 2002

(65) Prior Publication Data

US 2003/0203833 A1 Oct. 30, 2003

(51) Int. Cl.
*C12Q 1/68* (2006.01)

(52) U.S. Cl. ..... 435/6

(58) Field of Classification Search ..... 435/6
See application file for complete search history.

*Primary Examiner*—Michael J. Caronne
*Assistant Examiner*—Aileen Felton
(74) *Attorney, Agent, or Firm*—Virginia C. Bennett

(57) ABSTRACT

Polymorphisms in the cysteinyl-leukotriene receptor 2 gene and their association with asthma are described.

3 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIG. 1

```
aagttctcta agtttgaagc gtcagcttca accaaacaaa ttaatggcta ttctacattc   60
aaaaatcagg aaatttaaat ttattatgaa atgtaatgca gcatgtagta aagacttaac  120
cagtgtttta aaactcaact ttcaaagaaa agatagtatt gctccctgtt tcattaaaac  180
ctagagagat gtaatcagta agcaagaagg aaaaagggaa attcacaaag taactttttg  240
tgtctgtttc tttttaaccc agcatggaga gaaaatttat gtccttgcaa ccatccatct  300
ccgtatcaga aatggaacca aatggcacct tcagcaataa caacagcagg aactgcacaa  360
ttgaaaactt caagagagaa tttttcccaa ttgtatatct gataatattt ttctggggag  420
tcttgggaaa tgggttgtcc atatatgttt tcctgcagcc ttataagaag tccacatctg  480
tgaacgtttt catgctaaat ctggccattt cagatctcct gttcataagc acgcttccct  540
tcagggctga ctattatctt agaggctcca attggatatt tggagacctg gcctgcagga  600
ttatgtctta ttccttgtat gtcaacatgt acagcagtat ttatttcctg accgtgctga  660
gtgttgtgcg tttcctggca atggttcacc cctttcggct tctgcatgtc accagcatca  720
ggagtgcctg gatcctctgt gggatcatat ggatccttat catggcttcc tcaataatgc  780
tcctggacag tggctctgag cagaacggca gtgtcacatc atgcttagag ctgaatctct  840
ataaaattgc taagctgcag accatgaact atattgcctt ggtggtgggc tgcctgctgc  900
catttttcac actcagcatc tgttatctgc tgatcattcg ggttctgtta aaagtggagg  960
tcccagaatc ggggctgcgg gtttctcaca ggaaggcact gaccaccatc atcatcacct 1020
tgatcatctt cttcttgtgt ttcctgccct atcacacact gaggaccgtc cacttgacga 1080
catggaaagt gggtttatgc aaagacagac tgcataaagc tttggttatc acactggcct 1140
tggcagcagc caatgcctgc ttcaatcctc tgctctatta ctttgctggg gagaatttta 1200
aggacagact aaagtctgca ctcagaaaag gccatccaca gaaggcaaag acaaagtgtg 1260
ttttccctgt tagtgtgtgg ttgagaaagg aaacaagagt ataaggagct cttagatgag 1320
acctgttctt gtatccttgt gtccatcttc attcactcat agtctccaaa tgactttgta 1380
tttacatcac tcccaacaaa tgttgattct taatatttag ttgaccatta cttttgttaa 1440
taagacctac ttcaaaaatt ttattcagtg tattttcagt tgttgagtct taatgaggga 1500
tacaggagga aaaatcccta ctagagtcct gtgggctgaa atatcagact gggaaaaaat 1560
gcaaagcaca ttggatccta cttttcttca gatattgaac cagatctctg gcccatcagg 1620
ctttctaaat tcttcaaaag agccacaact tccccagctt ctccagctcc cctgtcctct 1680
tcaatccctt gagatatagc aactaacgac gctactggaa gccccagagc agaaaagaag 1740
cacatcctaa gattcaggga aagactaact gtgaaaagga aggctgtcct ataacaaagc 1800
agcatcaagt cccaagtaag gacagtgaga gaaaaggggg agaaggattg gagcaaaaga 1860
gaactggcaa taagtagggg aaggaagaat ttcattttgc attgggagag aggttctaac 1920
acactgaagg caaccctatt tctactgttt ctctcttgcc agggtattag gaaggacagg 1980
aaaagtagga ggaggatctg gggcattgcc ctaggaaatg aaagaattgt gtatagaatg 2040
gaagggggat catcaaggac atgtatctca aattttcttt gagatgcagg ttagttgacc 2100
ttgctgcagt tctccttccc attaattcat tgggatggaa gccaaaaata aaagaggtgc 2160
ctctgaggat tagggttgag cactcaaggg aaagatggag tagagggcaa atagcaaaag 2220
ttgttgcact cctgaaattc tattaacatt tccgcagaag atgagtaggg agatgctgcc 2280
ttccctttg agatagtgta gaaaaacact agatagtgtg agaggttcct ttctgtccat 2340
tgaaacaagg ctaaggatac taccaactac tatcaccatg accattgtac tgacaacaat 2400
tgaatgcagt ctccctgcag ggcagattat gccaggcact ttacatttgt tgatcccatt 2460
tgacattcac accaaagctc tgagttccat tttacagctg aagaaattga agcttagaga 2520
aattaagaag cttgtttaag tttacacagc tagtaagagt tttaaaaatc tctgtgcaga 2580
agtgttggct gggtgctctc cccaccacta cccttgtaaa cttccaggaa gattggttga 2640
aagtctgaat aaaagctgtc ctttcctacc aatttcctcc ccctcctcac tctcacaaga 2700
aaaccaaaag tttctcttca gagttgttga ctcatagtac agtaaagggt ggaggtgata 2760
tggcattctg aaagtaggga gggactaagt cagtcgtcat actaaacaaa aatcccagta 2820
ccctttcctt atttagctac cagaatgatg acagacagac tcaaaccctg tcaagacagg 2880
accctggagg atcctcctat ggggaaactg cataatctga aaaaaaggct gacagataca 2940
aatagttgag gatccttcaa cacaaaagct gcgtgtctgc cctattactc acctgacgat 3000
gaagcccaca atgcaacaaa tcccttccac tcacagcatt tggtcaacct gtcagagcct 3060
cattcttaat tatgaaaagt agtcaatgaa cacaatacat ttgagggaaa ggccgtaaca 3120
tgaaaggcac caacaaataa atgtgagagt agatagatac cttttgagta taaaagatcc 3180
tccaaaataa gagattaaac caagatagag gaaaacacag tagctgggaa acaaggaatc 3240
caacgcagga gaaagtgaag agaattccca ggatgttggt gtgtagcagg cttagaaagc 3300
```

FIG. 2

Met Glu Arg Lys Phe Met Ser Leu Gln Pro Ser Ile Ser Val Ser Glu Met Glu Pro Asn 20
Gly Thr Phe Ser Asn Asn Asn Ser Arg Asn Cys Thr Ile Glu Asn Phe Lys Arg Glu Phe 40
Phe Pro Ile Val Tyr Leu Ile Ile Phe Phe Trp Gly Val Leu Gly Asn Gly Leu Ser Ile 60
Tyr Val Phe Leu Gln Pro Tyr Lys Lys Ser Thr Ser Val Asn Val Phe Met Leu Asn Leu 80
Ala Ile Ser Asp Leu Leu Phe Ile Ser Thr Leu Pro Phe Arg Ala Asp Tyr Tyr Leu Arg 100
Gly Ser Asn Trp Ile Phe Gly Asp Leu Ala Cys Arg Ile Met Ser Tyr Ser Leu Tyr Val 120
Asn Met Tyr Ser Ser Ile Tyr Phe Leu Thr Val Leu Ser Val Val Arg Phe Leu Ala Met 140
Val His Pro Phe Arg Leu Leu His Val Thr Ser Ile Arg Ser Ala Trp Ile Leu Cys Gly 160
Ile Ile Trp Ile Leu Ile Met Ala Ser Ser Ile Met Leu Leu Asp Ser Gly Ser Glu Gln 180
Asn Gly Ser Val Thr Ser Cys Leu Glu Leu Asn Leu Tyr Lys Ile Ala Lys Leu Gln Thr 200
Met Asn Tyr Ile Ala Leu Val Val Gly Cys Leu Leu Pro Phe Phe Thr Leu Ser Ile Cys 220
Tyr Leu Leu Ile Ile Arg Val Leu Leu Lys Val Glu Val Pro Glu Ser Gly Leu Arg Val 240
Ser His Arg Lys Ala Leu Thr Thr Ile Ile Ile Thr Leu Ile Ile Phe Phe Leu Cys Phe 260
Leu Pro Tyr His Thr Leu Arg Thr Val His Leu Thr Thr Trp Lys Val Gly Leu Cys Lys 280
Asp Arg Leu His Lys Ala Leu Val Ile Thr Leu Ala Leu Ala Ala Ala Asn Ala Cys Phe 300
Asn Pro Leu Leu Tyr Tyr Phe Ala Gly Glu Asn Phe Lys Asp Arg Leu Lys Ser Ala Leu 320
Arg Lys Gly His Pro Gln Lys Ala Lys Thr Lys Cys Val Phe Pro Val Ser Val Trp Leu 340
Arg Lys Glu Thr Arg Val

ASSOCIATION OF ASTHMA WITH POLYMORPHISMS IN THE CYSTEINYL LEUKOTRIENE 2 RECEPTOR

FIELD OF THE INVENTION

The present invention relates to polymorphisms in the cysteinyl-leukotriene receptor 2 gene and asthma.

BACKGROUND OF THE INVENTION

Asthma is one of the most frequent chronic diseases with a prevalence of up to 10% (Jarvis and Burney, Br. Med. J. 316:607 (1988)). Both genetic and environmental factors contribute to the overall phenotype. Family studies have shown an increased frequency of asthma in first-degree relatives (Marsh, Allergol. Immunopathol. (Madr.) Suppl 9:60 (1981), Townley et al, J. Allergy Clin. Immunol. 77:101 (1986)). Environmental exposure to allergens, pollutants, and viral respiratory infections are important in the development of asthma (Boushey et al, Am. Rev. Respir. Dis. 121:389 (1980), Cookson and Moffat, Hum. Mol. Genet. 9:2359 (2000)). The interaction between the genetic and environmental factors in the pathogenesis of asthma is not fully understood. Asthma is the most common chronic childhood disease in developed nations and carries substantial direct and indirect economic cost (Lenny, Pediatr. Pulmonol. Suppl. 15:13 (1997)). The prevalence of asthma and other allergic diseases has risen over the past 2 decades (McNally, et al, Soc. Sci. Med. 46:729 (1998)) and the cost of treating the disease in United States is approximately US $6 billion per annum (Smith et al, Am. J. Respir. Crit. Care Med. 156:787 (1997)).

In view of the impact of asthma, better methods of identifying children at risk, and of assessing the efficacy of anti-asthma therapeis, would be beneficial.

SUMMARY OF THE INVENTION

A first aspect of the present invention is a method of identifying a subject at increased risk of asthma, by detecting the allelic forms of the A601G polymorphism in the Cysteinyl leukotriene 2 receptor gene. A person homozygous for the A allele is at increased risk for asthma compared to a subject with at least one G allele.

BRIEF DESCRIPTION OF THE FIGURES

FIG. 1 provides the sequence of the CysLT2 receptor gene (SEQ ID NO:1), with the start codon underlined (264–266) and stop codon underlined (1302–1304). The polymorphic sites are indicated by bold underlined text: coding SNP A601G (864), noncoding SNP TSC3P1 (A/G at 2796) and TSC3P2 (A/G at 2960).

FIG. 2 provides the amino acid sequence (SEQ ID NO:2) encoded by the above nucleotide sequence, with the polymorphic amino acid (met/val) shown in bold underlined text.

DETAILED DESCRIPTION

Leukotrienes are a family of eicosinoids which form part of a much larger group of compounds synthesized from arachadonic acid. The cysteinyl leukotrienes (CysLTs), LTC4, LTD4, and LTE4, previously known as slow reacting substance of anaphylaxis, or SRS-A, are derived from arachidonic acid via oxygenation and dehydration by 5-lipoxygenase followed by specific glutathione addition by LTC4 synthase.

The CysLTs mediate their biological actions through two pharmacologically defined G-protein-coupled receptors (GPCRs), named the CysLT1 and CysLT2 receptors. (See WO 01/59105 (Glaxo Group Limited); Nicosia, Monaldi Arch. Chest Dis. 54:242 (1999); Takasaki et al., Biochem. Biophys Res. Commun. 274:316 (2000); Heise et al., J. Biol. Chem. 275:30531 (2000); Nothacker et al., Mol. Pharmacol. 58:1601 (2000); Nicosia et al., Pulm. Pharmacol. Ther. 14:3 (2001)). $LTB_4$ is produced mainly by macrophages and neutrophils and stimulates neutrophil chemotaxis, enhances neutrophil-endothelial cell interactions and stimulates neutrophil activation leading to degranulation and the release of mediators, enzymes and superoxides. The cysteinyl leukotriene receptors respond to $LTD_4$, $LTE_4$, $LTC_4$ and $LTF_4$, however the occurrence in vivo of $LTF_4$ is unclear.

Cysteinyl leukotrienes contract airway smooth muscle, increase microvascular permeability, stimulate mucus secretion, decrease mucociliary clearance and recruit eosinophils into the airways. The CysLT2 receptor has been documented pharmacologically to be expressed in guinea pig trachea and ileum, ferret trachea and spleen, sheep bronchus, and human pulmonary and saphenous vein preparations. At the CysLT2 receptor subtype, the agonist potency rank order is LTC4=LTD4>>LTE4 and LTE4 is a partial agonist.CysLT1 receptor-specific leukotriene receptor antagonists, such as montelukast, zafirlukast and pranlukast are currently used to control bronchoconstriction and inflammation in asthmatic patients. CysLT1 is mainly detected in lung smooth muscle cells, macrophages, spleen and peripheral blood lymphocytes and has not been detected in heart.

As used herein, a "genetic subset" of a population consists of those members of the population having a particular genotype. In the case of a biallelic polymorphism, a population can potentially be divided into three subsets: homozygous for allele 1 (1,1), heterozygous (1,2), and homozygous for allele 2 (2,2). A 'population' of subjects may be defined using various criteria, e.g., individuals being treated with a certain therapeutic or diagnosed with a certain medical condition, individuals of a defined ethnicity or demographic group, etc.

As used herein, a subject that is "predisposed to" or "at increased risk of" a particular phenotypic response based on genotyping will be more likely to display that phenotype than an individual with a different genotype at the target polymorphic locus (or loci).

"Genetic testing" (also called genetic screening) as used herein refers to the testing of a biological sample from a subject to determine the subject's genotype; and may be utilized to determine if the subject's genotype comprises alleles that either cause, or increase susceptibility to, a particular phenotype (or that are in linkage disequilibrium with allele(s) causing or increasing susceptibility to that phenotype).

"Linkage disequilibrium" refers to the tendency of specific alleles at different genomic locations to occur together more frequently than would be expected by change. Alleles at given loci are in complete equilibrium if the frequency of any particular set of alleles (or haplotype) is the product oftheir individual population frequencies A commonly used measure of linkage disequilibrium is r:

$$r = \frac{\hat{\Delta}_{AB}}{\sqrt{(\tilde{\pi}_A + \hat{D}_A)(\tilde{\pi}_B + \hat{D}_B)}}$$

where $$\tilde{\pi}_A = \tilde{p}_A(1-\tilde{p}_A),\ \tilde{\pi}_B = \tilde{p}_B(1-\tilde{p}_B),\ \hat{D}_A = \tilde{P}_{AA} - \tilde{p}_A^2,\ \hat{D}_B = \tilde{P}_{BB} - \tilde{p}_B^2$$

$$\hat{\Delta}_{AB} = \frac{1}{n} n_{AB} - 2\tilde{p}_A\tilde{p}_B$$

$nr^2$ has an approximate chi square distribution with 1 degree freedom for biallelic markers. Loci exhibiting an r such that $nr^2$ is greater than 3.84, corresponding to a significant chi-squared statistic at the 0.05 level, are considered to be in linkage disequilibrium (BS Weir 1996 Genetic Data Analysis II Sinauer Associates, Sunderland, MD).

Alternatively, a normalized measure of linkage disequilibrium can be defined as:

$$D'_{AB} = \begin{cases} \dfrac{D_{AB}}{\min(p_A p_B,\ p_a p_b)}, & D_{AB} < 0 \\ \dfrac{D_{AB}}{\min(p_A p_b,\ p_a p_B)}, & D_{AB} > 0 \end{cases}$$

The value of the D' has a range of −1.0 to 1.0. When statistically significant absolute D' value for two markers is not less than 0.3 they are considered to be in linkage disequilibrium.

The present studies investigated the presence of three polymorphisms in the CysLT2 receptor gene, and the occurrence of asthma.

Sample Composition and Clinical Evaluation

Asthma families were studied at 2 collection centers: (1) the Department of Medicine, University of Minnesota Medical School, Minneapolis, Minn. (Min); and (2) Department of Respiratory Medicine, Hvidovre University Hospital, DK-2650 Hvidovre, Denmark (Den). In the selection of these families, at least two siblings with clinical asthma were required. The proband had the following criteria for the diagnosis of asthma: (1) at least 2 out of the 3 categories including of cough, wheezing, and dyspnoea should be recurrent and (2) a documentation of an increase in FEV by 15% of predicted value, minimum 300 ml) after a bronchodilator or (b) a positive methacholine inhalation challenge ($PC_{20}$ $FEV_1$<10 mg/ml). The following exclusion criteria were followed:

1. Birth weight less than 4.4 pounds;
2. Systematic vasculitis involving the lungs;
3. Congenital or acquired pulmonary diseases at birth;
4. Uncorrected congenital heart disease;
5. Severe cardiac disease;
6. Current medications that interfered with phenotypes that could not be stopped, such as beta blocking agents;
7. Isolated occupation induced asthma.

All subjects were evaluated by using standard protocols. Baseline spirometry was performed by according to American Thoracic Society (ATS) criteria. Skin Prick Tests (SPT) for the common allergens (mites, animal, insects, pollen and mould) were conducted.

The Denmark collection was composed of 268 families, 985 samples with genotypes, 367 children with Physician's diagnosis of asthma (PDA), 120 with Bronchial hyperreactivity (BHR) and 275 with atopic asthma. The Minnesota collection constituted 83 Caucasian families, 317 samples with genotypes, 168 children with PDA, 144 with strict asthma, 122 with BHR and 139 with atopic asthma.

In addition to the family samples, a matched Caucasian case control collection from North Carolina was also evaluated (one hundred cases and 100 controls, "asthma-1" collection). This collection is from Duke University Medical Center, Durham, N.C. The primary diagnostic criteria for this collection was a definite physician's diagnosis for the presence of asthma (PDA) or not asthma. Skin prick tests to common allergens and standard spirometric measurements were also evaluated in this collection.

Phenotypes

The following phenotypes were evaluated. 1) PDA; 2) strict asthma, 2 or more classic symptoms (cough, wheeze and shortness of breath) and a positive methacholine challenge test or bronchodilator reversibility; 3) bronchial hyperreactivity (BHR), positive methacholine response at or below 10 mg/ml of methacholine and 4) atopic asthma, physician's diagnosis and positive results on at least one skin allergen tests.

Genotyping

DNA was isolated from whole blood or lymphoblastoid cell lines. The Single Nucleotide Polymorphisms (SNP) genotypes were generated using the 5' nuclease assay with TaqMan® (Applied Biosystems, Foster City, Calif.) fluorogenic probes and the products were read on an ABI PRISM® 7700 Sequence Detection System (Applied Biosystems).

Statistical Analysis

The association of the asthma related phenotypes with the markers are tested by transmission disequilibrium test comparing the frequencies of the alleles transmitted to affected children to those not transmitted using *Transmit* (Dudbridge et al, Am. J. Hum. Genet. 66:2009 (2000)), for the family data. Association analysis for the case control population was done using Fisher's exact test (Zaykin et al, Genetica 96:169 (1995)). Haplotype analysis of the family data was done using Transmit (Dudbridge et al, 2000) and by a method using EM algorithm for the case control data (Zaykin et al, "Testing association of statiscally inferred haplotypes with discrete and continuous traits in samples of unrelated individuals, Human Heredity (in press)).

Hardy-Weinberg Equilibrium (HWE) Analysis

The departure from HWE is tested using a Chi square test, by testing the difference between the expected (calculated from the allele frequencies) and observed genotype frequencies.

Linkage Disequilibrium (LD) Analysis

The LD between two markers is given by $D_{AB}=p_{AB}-p_A p_B$, where $p_A$ is the allele frequency of A allele of the first marker, $_{pB}$ is the allele frequency of $_B$ allele of the second marker, and $p_{AB}$ is the joint frequency of alleles A and B on the same haplotype. A commonly used measure of LD can be calculated as follows.

Where $$\hat{\Delta}_{AB} = \frac{1}{n} n_{AB} - 2\tilde{p}_A \tilde{p}_B$$

$$r = \frac{\hat{\Delta}_{AB}}{\sqrt{(\tilde{\pi}_A + \hat{D}_A)(\tilde{\pi}_B + \hat{D}_B)}}$$

$nr^2$ has an approximate chi square distribution with 1 df.

According to the present methods, a compound may be screened for variation in its effectiveness in treating asthma among genetic subpopulations of subjects. The phenotypic response of subjects to an asthma treatment may include the magnitude, duration, or occurrence of a positive response to treatment, or the magnitude, duration or occurrence of an unwanted side effect, or the absence of any response. Methods of correlating genotype with phenotypic response to treatment include administering the therapeutic to a population of subjects, obtaining biological samples from the subjects, genotyping polymorphic allelic sites as identified herein, and correlating the genotype of the subjects with their phenotypic response (e.g., response to therapeutic treatment).

Polymorphic alleles may be detected by determining the DNA polynucleotide sequence, or by detecting the corresponding sequence in RNA transcripts from the polymorphic gene, or where the nucleic acid polymorphism results in a change in an encoded protein by detecting such amino acid sequence changes in encoded proteins; using any suitable technique as is known in the art. Polynucleotides utilized for typing are typically genomic DNA, or a polynucleotide fragment derived from a genomic polynucleotide sequence, such as in a library made using genomic material from the individual (e.g. a cDNA library). The polymorphism may be detected in a method that comprises contacting a polynucleotide or protein sample from an individual with a specific binding agent for the polymorphism and determining whether the agent binds to the polynucleotide or protein, where the binding indicates that the polymorphism is present. The binding agent may also bind to flanking nucleotides and amino acids on one or both sides of the polymorphism, for example at least 2, 5, 10, 15 or more flanking nucleotide or amino acids in total or on each side. In the case where the prescence of the polymorphism is being determined in a polynucleotide it may be detected in the double stranded form, but is typically detected in the single stranded form.

As is well known genetics, nucleotide and amino acid sequences obtained from different sources for the same gene may vary both in the numbering scheme and in the precise sequence. Such differences may be due to inherent sequence variability within the gene and/or to sequencing errors. Accordingly, reference herein to a particular polymorphic site by number (e.g., CysLT2R A601G) will be understood by those of skill in the art to include those polymorphic sites that correspond in sequence and location within the gene, even where different numbering/nomenclature schemes are used to describe them.

EXAMPLE 1: PRIMERS AND PROBES

Marker Name: CysLT2R 3P1 (A>G)

Alelle 1=A

Allele 2=G

Probes:

allele 1=6FAM-ACTAAGTCAGTCATCATACTAAACAAAAATCC-TAMRA (SEQ ID NO:3)

allele 2=VIC-ACTAAGTCAGTCGTCATACTAAACAAAAATC-TAMRA (SEQ ID NO:4)

Primers:

CysLT2R 3P1 A>G F GGGTGGAGGTGATATGGCATT (SEQ ID NO:5)

CysLT2R3P1 A>G R TCTGTCTGTCATCATTCTGGTAGCT (SEQ ID NO:6)

All probes and primers were suppled at 100 uM in water.

Marker Name: CysLT2R 3P2 (A>G)

Allele 1=A.

Allele 2=G.

Probes:

allele 1=6FAM-TTGAGGATCCTTCAACACAAAAGCTGC-TAMRA (SEQ ID NO:7)

allele 2=VIC-TTGAGGATCCTTCAGCACAAAAGCTG-TAMRA (SEQ ID NO:8)

Primers:

CysLT2R 3P2 A>G F AGACAGACTCAAACCCTGTCAAGAC (SEQ ID NO:9)

CysLT2R3P2 A>G R GCTTCATCGTCAGGTGAGTAATAGG (SEQ ID NO:10)

All probes and primers were supplied at 100 uM in water.

Marker Name: CysLT2R A601G (CysLT2R Met201Val)

Allele 1=A

Allele 2=G

Probes:

allele 1=6FAM-TGCTAAGCTGCAGACCATGAACTATATTGC-TAMRA (SEQ ID NO:11)

allele 2=VIC-CTAAGCTGCAGACCGTGAACTATATTGCC-TAMRA (SEQ ID NO:12)

Primers:

CysLT2R A601G A>G F CACATCATGCTTAGAGCTGAATCTC (SEQ ID NO:13)

CysLT2R A601G A>G R CAGATAACAGATGCTGAGTGTGAAAA (SEQ ID NO:14)

All probes and primers were supplied at 100 uM in water.

EXAMPLE 2: RESULTS

The above three markers were genotyped in the Denmark, Minnesota and asthma-1 collections, in the Cyslt2R gene. One coding polymorphism (A601G), and 2 noncoding SNPS (TSC3P1 and TSC3P2) that are 3' to the coding polymorphism were genotyped.

Populations studied (1) Minnesota: 91 families (2) Denmark: 268 familes (3) Asthma-1: 200 cases and 100 controls (Phenotype PDA)

Den-Min: Combined analysis from Denmark and Minnesota.

The frequencies of different alleles are provided in Table 1 and the results of the association study are provided in Table 2. The allele frequency of CYSLT2R_A601G in Parents with and without asthma in the Denmark and Minnesota populations is shown in Table 3; in the Asthma-1 population, in Table 4. Table 5 shows linkage disequilibrium estimates.

Results and Discussion

The transmission dis-equilibrium test showed significantly lower transmission of the G allele of the marker A601G to the asthmatic children. This association was statistically significant in the combined Denmark and Minnesota families for physician's diagnosis of asthma (PDA), atopic asthma, and strict definition of asthma. The association was statistically significant in the Denmark families for PDA and marginally significant for atopic asthma. The frequency of the G allele was lower in asthmatics compared to non-asthmatics in the asthma-1 case control collection. The affected and un-affected parents (for PDA) from the Denmark and Minnesota collections were examined, and it was found that the frequency of the G allele was lower in affected parents compared to unaffected parents. The markers A601G and CYSLT2R-3P1 are in significant linkage dis-equilibrium (see Table 5) and the haplotype involving the allele G of A601G and allele A of CYSLT2R-3P1 shows significantly lower transmission to the affected children in the combined Minnesota and Denmark families for PDA (p=0.0032).

The A601G single nucleotide polymorphism was found to be associated with Asthma and related phenotypes, and does change the amino acid sequence of CysLt2R from Methionine to Valine at amino acid position 201. The G allele of this polymorphism was found to be associated with resistance to asthma. This polymorphism has been associated with decreased expression of the CysLT2R protein, and also the decreased affinity for leukotrienes to the receptor. This association suggests that compounds that block the CysLT2R receptor are useful for the treatment of asthma.

TABLE-1

Frequency of the Alleles in Different Populations

| Marker | Allele | Minnesota | Denmark | DenMin | Asthma-1 | Pooled |
|---|---|---|---|---|---|---|
| CYSLT2R_3P1 | A | 0.56 | 0.53 | 0.54 | 0.56 | 0.55 |
| CYSLT2R_3P1 | G | 0.44 | 0 47 | 0.46 | 0.44 | 0.45 |
| CYSLT2R_3P2 | A | 0.93 | 0 94 | 0.94 | 0.93 | 0.94 |
| CYSLT2R_3P2 | G | 0.07 | 0.06 | 0.06 | 0.07 | 0.06 |
| CYSLT2R_A601G | A | 0.97 | 0.97 | 0.97 | 0.98 | 0.97 |
| CYSLT2R_A601G | G | 0.03 | 0.03 | 0.03 | 0.02 | 0.03 |

TABLE-2

Results of the Association Study

| | Phenotype | | | | Population |
|---|---|---|---|---|---|
| Marker | ASTHMA | ATP_ASTH | BHR | PDA | Minnesota |
| CYSLT2R_3P1 | 0.315 | 0.307 | 0.874 | 0.676 | Minnesota |
| CYSLT2R_3P2 | 0.295 | 0.520 | 0.822 | 0.528 | Minnesota |
| CYSLT2R_A601G | 0.092 | 0.435 | 0.472 | 0.138 | Minnesota |
| CYSLT2R_3P1 | 0.817 | 0.777 | 0.416 | 0.846 | Denmark |
| CYSLT2R_3P2 | 0.610 | 0.392 | 0.743 | 0.132 | Denmark |
| CYSLT2R_A601G | 0.179 | 0.057 | 0.100 | 0.009 | Denmark |
| CYSLT2R_3P1 | 0.535 | 0.567 | 0.576 | 0.901 | Den-Min |
| CYSLT2R_3P2 | 0.651 | 0.875 | 0.961 | 0.522 | Den-Min |
| CYSLT2R_A601G | 0.037 | 0.042 | 0.102 | 0.002 | Den-Min |
| CYSLT2R_3P1 | | | | 0.77 | Asthma-1 |
| CYSLT2R_3P2 | | | | 0.12 | Asthma-1 |
| CYSLT2R_A601G | | | | 0.31 | Asthma-1 |

TABLE 3

Allele Frequency of CYSLT2R_A601G in Parents with Asthma or without Asthma (Denmark and Minnesota)

| Asthma (PDA) | Number | A/G | G/G | Frequency of G allele |
|---|---|---|---|---|
| NO | 457 | 30 | 0 | 3.28 |

TABLE 3-continued

Allele Frequency of CYSLT2R_A601G in Parents with Asthma or without Asthma (Denmark and Minnesota)

| Asthma (PDA) | Number | A/G | G/G | Frequency of G allele |
|---|---|---|---|---|
| YES | 142 | 5 | 1 | 2.46 |

TABLE 4

Allele frequency of CYSLT2R_A601G in individuals with asthma or without asthma (Asthma-1)

| Asthma (PDA) | Number | A/G | G/G | Frequency of G allele |
|---|---|---|---|---|
| NO | 100 | 5 | 0 | 2.50 |
| YES | 200 | 5 | 0 | 1.25 |

TABLE 5

Linkage Disequilibrium Estimates

| | Marker1 | Marker2 | Chi Squared | p Value (Chi Sq.) | LD Correlation R |
|---|---|---|---|---|---|
| Minnesota | CYSLT2R_3P1 | CYSLT2R_3P2 | 14.281 | 0.000157443 | 0.304523 |
| | CYSLT2R_3P1 | CYSLT2R_A601G | 11.0162 | 0.000903191 | 0.266594 |
| | CYSLT2R_3P2 | CYSLT2R_A601G | 1.63404 | 0.201141 | 0.102019 |
| Denmark | CYSLT2R_3P1 | CYSLT2R_3P2 | 41.0963 | 1.45E−10 | 0.297928 |
| | CYSLT2R_3P1 | CYSLT2R_A601G | 4.09937 | 0.0428993 | 0.0938927 |
| | CYSLT2R_3P2 | CYSLT2R_A601G | 3.63906 | 0.0564388 | 0.087899 |
| DenMin | CYSLT2R_3P1 | CYSLT2R_3P2 | 55.067 | 1.16E−13 | 0.298747 |
| | CYSLT2R_3P1 | CYSLT2R_A601G | 12.288 | 0.000455885 | 0.140781 |
| | CYSLT2R_3P2 | CYSLT2R_A601G | 5.24756 | 0.0219776 | 0.0914111 |
| Asthma-1 | CYSLT2R_3P1 | CYSLT2R_3P2 | 35.643 | 2.37E−09 | 0.348782 |
| | CYSLT2R_3P1 | CYSLT2R_A601G | 4.69565 | 0.0302391 | 0.126811 |
| | CYSLT2R_3P2 | CYSLT2R_A601G | 0.275975 | 0.599352 | 0.0303808 |
| Pooled | CYSLT2R_3P1 | CYSLT2R_3P2 | 89.9028 | 2.50E−21 | 0.314316 |
| | CYSLT2R_3P1 | CYSLT2R_A601G | 16.4589 | 4.97E−05 | 0.134339 |
| | CYSLT2R_3P2 | CYSLT2R_A601G | 3.22997 | 0.0723019 | 0.0590282 |

SEQUENCE LISTING

```
<160> NUMBER OF SEQ ID NOS: 14

<210> SEQ ID NO 1
<211> LENGTH: 3300
<212> TYPE: DNA
```

-continued

```
<213> ORGANISM: Homo sapiens
<220> FEATURE:
<221> NAME/KEY: CDS
<222> LOCATION: (264)..(1304)
<223> OTHER INFORMATION:

<400> SEQUENCE: 1

aagttctcta agtttgaagc gtcagcttca accaaacaaa ttaatggcta ttctacattc     60

aaaaatcagg aaatttaaat ttattatgaa atgtaatgca gcatgtagta aagacttaac    120

cagtgtttta aaactcaact ttcaaagaaa agatagtatt gctccctgtt tcattaaaac    180

ctagagagat gtaatcagta agcaagaagg aaaaagggaa attcacaaag taactttttg    240

tgtctgtttc tttttaaccc agc atg gag aga aaa ttt atg tcc ttg caa cca    293
                          Met Glu Arg Lys Phe Met Ser Leu Gln Pro
                          1               5                   10

tcc atc tcc gta tca gaa atg gaa cca aat ggc acc ttc agc aat aac      341
Ser Ile Ser Val Ser Glu Met Glu Pro Asn Gly Thr Phe Ser Asn Asn
                15                  20                  25

aac agc agg aac tgc aca att gaa aac ttc aag aga gaa ttt ttc cca      389
Asn Ser Arg Asn Cys Thr Ile Glu Asn Phe Lys Arg Glu Phe Phe Pro
            30                  35                  40

att gta tat ctg ata ata ttt ttc tgg gga gtc ttg gga aat ggg ttg      437
Ile Val Tyr Leu Ile Ile Phe Phe Trp Gly Val Leu Gly Asn Gly Leu
        45                  50                  55

tcc ata tat gtt ttc ctg cag cct tat aag aag tcc aca tct gtg aac      485
Ser Ile Tyr Val Phe Leu Gln Pro Tyr Lys Lys Ser Thr Ser Val Asn
    60                  65                  70

gtt ttc atg cta aat ctg gcc att tca gat ctc ctg ttc ata agc acg      533
Val Phe Met Leu Asn Leu Ala Ile Ser Asp Leu Leu Phe Ile Ser Thr
75                  80                  85                  90

ctt ccc ttc agg gct gac tat tat ctt aga ggc tcc aat tgg ata ttt      581
Leu Pro Phe Arg Ala Asp Tyr Tyr Leu Arg Gly Ser Asn Trp Ile Phe
                95                  100                 105

gga gac ctg gcc tgc agg att atg tct tat tcc ttg tat gtc aac atg      629
Gly Asp Leu Ala Cys Arg Ile Met Ser Tyr Ser Leu Tyr Val Asn Met
            110                 115                 120

tac agc agt att tat ttc ctg acc gtg ctg agt gtt gtg cgt ttc ctg      677
Tyr Ser Ser Ile Tyr Phe Leu Thr Val Leu Ser Val Val Arg Phe Leu
        125                 130                 135

gca atg gtt cac ccc ttt cgg ctt ctg cat gtc acc agc atc agg agt      725
Ala Met Val His Pro Phe Arg Leu Leu His Val Thr Ser Ile Arg Ser
    140                 145                 150

gcc tgg atc ctc tgt ggg atc ata tgg atc ctt atc atg gct tcc tca      773
Ala Trp Ile Leu Cys Gly Ile Ile Trp Ile Leu Ile Met Ala Ser Ser
155                 160                 165                 170

ata atg ctc ctg gac agt ggc tct gag cag aac ggc agt gtc aca tca      821
Ile Met Leu Leu Asp Ser Gly Ser Glu Gln Asn Gly Ser Val Thr Ser
                175                 180                 185

tgc tta gag ctg aat ctc tat aaa att gct aag ctg cag acc atg aac      869
Cys Leu Glu Leu Asn Leu Tyr Lys Ile Ala Lys Leu Gln Thr Met Asn
            190                 195                 200

tat att gcc ttg gtg gtg ggc tgc ctg ctg cca ttt ttc aca ctc agc      917
Tyr Ile Ala Leu Val Val Gly Cys Leu Leu Pro Phe Phe Thr Leu Ser
        205                 210                 215

atc tgt tat ctg ctg atc att cgg gtt ctg tta aaa gtg gag gtc cca      965
Ile Cys Tyr Leu Leu Ile Ile Arg Val Leu Leu Lys Val Glu Val Pro
    220                 225                 230

gaa tcg ggg ctg cgg gtt tct cac agg aag gca ctg acc acc atc atc     1013
Glu Ser Gly Leu Arg Val Ser His Arg Lys Ala Leu Thr Thr Ile Ile
235                 240                 245                 250
```

-continued

```
atc acc ttg atc atc ttc ttc ttg tgt ttc ctg ccc tat cac aca ctg     1061
Ile Thr Leu Ile Ile Phe Phe Leu Cys Phe Leu Pro Tyr His Thr Leu
                255                 260                 265

agg acc gtc cac ttg acg aca tgg aaa gtg ggt tta tgc aaa gac aga     1109
Arg Thr Val His Leu Thr Thr Trp Lys Val Gly Leu Cys Lys Asp Arg
            270                 275                 280

ctg cat aaa gct ttg gtt atc aca ctg gcc ttg gca gca gcc aat gcc     1157
Leu His Lys Ala Leu Val Ile Thr Leu Ala Leu Ala Ala Ala Asn Ala
        285                 290                 295

tgc ttc aat cct ctg ctc tat tac ttt gct ggg gag aat ttt aag gac     1205
Cys Phe Asn Pro Leu Leu Tyr Tyr Phe Ala Gly Glu Asn Phe Lys Asp
    300                 305                 310

aga cta aag tct gca ctc aga aaa ggc cat cca cag aag gca aag aca     1253
Arg Leu Lys Ser Ala Leu Arg Lys Gly His Pro Gln Lys Ala Lys Thr
315                 320                 325                 330

aag tgt gtt ttc cct gtt agt gtg tgg ttg aga aag gaa aca aga gta     1301
Lys Cys Val Phe Pro Val Ser Val Trp Leu Arg Lys Glu Thr Arg Val
                335                 340                 345

taa ggagctctta gatgagacct gttcttgtat ccttgtgtcc atcttcattc          1354

actcatagtc tccaaatgac tttgtattta catcactccc aacaaatgtt gattcttaat   1414

atttagttga ccattacttt tgttaataag acctacttca aaaattttat tcagtgtatt   1474

ttcagttgtt gagtcttaat gagggataca ggaggaaaaa tccctactag agtcctgtgg   1534

gctgaaatat cagactggga aaaaatgcaa agcacattgg atcctacttt tcttcagata   1594

ttgaaccaga tctctggccc atcaggcttt ctaaattctt caaaagagcc acaacttccc   1654

cagcttctcc agctcccctg tcctcttcaa tcccttgaga tatagcaact aacgacgcta   1714

ctggaagccc cagagcagaa aagaagcaca tcctaagatt cagggaaaga ctaactgtga   1774

aaaggaaggc tgtcctataa caaagcagca tcaagtccca agtaaggaca gtgagagaaa   1834

agggggagaa ggattggagc aaaagagaac tggcaataag taggggaagg aagaatttca   1894

ttttgcattg ggagagaggt tctaacacac tgaaggcaac cctatttcta ctgtttctct   1954

cttgccaggg tattaggaag gacaggaaaa gtaggaggag gatctggggc attgccctag   2014

gaaatgaaag aattgtgtat agaatggaag ggggatcatc aaggacatgt atctcaaatt   2074

ttctttgaga tgcaggttag ttgaccttgc tgcagttctc cttcccatta attcattggg   2134

atggaagcca aaaataaaag aggtgcctct gaggattagg gttgagcact caagggaaag   2194

atggagtaga gggcaaatag caaaagttgt tgcactcctg aaattctatt aacatttccg   2254

cagaagatga gtagggagat gctgccttcc cttttgagat agtgtagaaa aacactagat   2314

agtgtgagag gttcctttct gtccattgaa acaaggctaa ggatactacc aactactatc   2374

accatgacca ttgtactgac aacaattgaa tgcagtctcc ctgcagggca gattatgcca   2434

ggcactttac atttgttgat cccatttgac attcacacca aagctctgag ttccatttta   2494

cagctgaaga aattgaagct tagagaaatt aagaagcttg tttaagttta cacagctagt   2554

aagagtttta aaaatctctg tgcagaagtg ttggctgggt gctctcccca ccactaccct   2614

tgtaaacttc caggaagatt ggttgaaagt ctgaataaaa gctgtccttt cctaccaatt   2674

tcctcccccct cctcactctc acaagaaaac caaaagtttc tcttcagagt tgttgactca   2734

tagtacagta aagggtggag gtgatatggc attctgaaag tagggaggga ctaagtcagt   2794

cgtcatacta aacaaaaatc ccagtaccct ttccttattt agctaccaga atgatgacag   2854

acagactcaa accctgtcaa gacaggaccc tggaggatcc tcctatgggg aaactgcata   2914
```

-continued

```
atctgaaaaa aaggctgaca gatacaaata gttgaggatc cttcaacaca aaagctgcgt   2974

gtctgcccta ttactcacct gacgatgaag cccacaatgc aacaaatccc ttccactcac   3034

agcatttggt caacctgtca gagcctcatt cttaattatg aaaagtagtc aatgaacaca   3094

atacatttga gggaaaggcc gtaacatgaa aggcaccaac aaataaatgt gagagtagat   3154

agataccttt tgagtataaa agatcctcca aaataagaga ttaaaccaag atagaggaaa   3214

acacagtagc tgggaaacaa ggaatccaac gcaggagaaa gtgaagagaa ttcccaggat   3274

gttggtgtgt agcaggctta gaaagc                                        3300


<210> SEQ ID NO 2
<211> LENGTH: 346
<212> TYPE: PRT
<213> ORGANISM: Homo sapiens

<400> SEQUENCE: 2

Met Glu Arg Lys Phe Met Ser Leu Gln Pro Ser Ile Ser Val Ser Glu
1               5                   10                  15

Met Glu Pro Asn Gly Thr Phe Ser Asn Asn Asn Ser Arg Asn Cys Thr
            20                  25                  30

Ile Glu Asn Phe Lys Arg Glu Phe Phe Pro Ile Val Tyr Leu Ile Ile
        35                  40                  45

Phe Phe Trp Gly Val Leu Gly Asn Gly Leu Ser Ile Tyr Val Phe Leu
    50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                85                  90                  95

Tyr Tyr Leu Arg Gly Ser Asn Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Ala Asn Ala Cys Phe Asn Pro Leu Leu
    290                 295                 300
```

-continued

```
Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345


<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3

actaagtcag tcatcatact aaacaaaaat cc                                  32


<210> SEQ ID NO 4
<211> LENGTH: 31
<212> TYPE: DNA
<213> ORGANISM: Artificial Sequence
<220> FEATURE:
<223> OTHER INFORMATION: Synthetic Construct

<400> SEQUENCE: 4

actaagtcag tcgtcatact aaacaaaaat c                                   31


<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5

gggtggaggt gatatggcat t                                              21


<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6

tctgtctgtc atcattctgg tagct                                          25


<210> SEQ ID NO 7
<211> LENGTH: 27
<212> TYPE: DNA
<213> ORGANISM: Artificial Sequence
<220> FEATURE:
<223> OTHER INFORMATION: Synthetic Construct

<400> SEQUENCE: 7

ttgaggatcc ttcaacacaa aagctgc                                        27


<210> SEQ ID NO 8
<211> LENGTH: 26
<212> TYPE: DNA
<213> ORGANISM: Artificial Sequence
<220> FEATURE:
<223> OTHER INFORMATION: Synthetic Construct

<400> SEQUENCE: 8
```

-continued ttgaggatcc ttcagcacaa aagctg 26

<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9 agacagactc aaaccctgtc aagac 25

<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10 gcttcatcgt caggtgagta atagg 25

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct

<400> SEQUENCE: 11 tgctaagctg cagaccatga actatattgc 30

<210> SEQ ID NO 12
<211> LENGTH: 29
<212> TYPE: DNA
<213> ORGANISM: Artificial Sequence
<220> FEATURE:
<223> OTHER INFORMATION: Synthetic Construct

<400> SEQUENCE: 12 ctaagctgca gaccgtgaac tatattgcc 29

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13 cacatcatgc ttagagctga atctc 25

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14 cagataacag atgctgagtg tgaaaa 26

That which is claimed is:

1. A method of identifying a subject at increased risk of asthma, comprising detecting the allelic forms of the A601G polymorphism in the Cysteinyl leukotriene 2 receptor gene, where a person homozygous for the A allele is at increased risk for asthma compared to a subject with at least one G allele.

2. A method according to claim 1 where the subject is a member of a family having at least one member diagnosed with asthma.

3. A method of stratifying a population receiving pharmaceutical treatment for asthma to detect differences in phenotypic response to the pharmaceutical treatment, by:

(a) genotyping a population of subjects in need of pharmaceutical treatment for asthma, to determine each subject's allelic forms of the A601G polymorphism in the Cysteinyl leukotrine 2 receptor gene;

(b) administering to said subjects a pharmaceutical treatment for asthma;

(c) correlating each subject's phenotypic response to treatment with the subject's genotype, to detect phenotypic responses that are associated with said allelic forms.

* * * * *